US00PP19749P2

(12) United States Plant Patent
Gutter

(10) Patent No.: US PP19,749 P2
(45) Date of Patent: Feb. 17, 2009

(54) ***GAILLARDIA* PLANT NAMED 'GRANORAN'**

(50) Latin Name: *Gaillardia aristata*
Varietal Denomination: Granoran

(75) Inventor: Martien Everett Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/977,077

(22) Filed: Oct. 23, 2007

(51) Int. Cl.
*A01H 5/00* (2006.01)

(52) U.S. Cl. ..... Plt./431

(58) Field of Classification Search ..... Plt./431
See application file for complete search history.

*Primary Examiner*—Annette H Para
(74) *Attorney, Agent, or Firm*—S. Matthew Edwards

(57) ABSTRACT

A new *Gaillardia* plant, particularly distinguished by its orange-yellow flower color, early flowering without cold induction, and compact plant habit.

1 Drawing Sheet

Latin name of the genus and species of the plant claimed: *Gaillardia aristata.*
Varietal denomination: 'Granoran'.

BACKGROUND OF THE NEW PLANT

The present invention comprises a new distinct cultivar of *Gaillardia,* botanically known as *Gaillardia aristata.*

The new *Gaillardia* was not discovered but is a product of a planned breeding program conducted in Enkhuizen, Netherlands. The new *Gaillardia* cultivar is early flowering, has a compact plant habit, and an orange-yellow flower color.

The new *Gaillardia* is propagated by cuttings resulting from a single seedling. This seedling from a selection in *Gaillardia aristata* 'Burgundy' (not patented), identified as number 'F3351.' 'Burgundy' is a seed strain. A plant was selected in this strain and the seeds of this plant were harvested in the field. The female parent is known and the male parent is a "cloud" of pollen of the other plants. These seeds were sown and the same cycle was done: in this population one plant was selected and harvested, so pollinated again with a "cloud" of pollen. A third cycle was done the same way and the final seedling was selected. This took place from August 2000 until July 2002 in Enkhuizen, Netherlands. The seedling was selected in July 2003 in Enkhuizen in field conditions.

The present cultivar has been repeatedly asexually reproduced by cuttings in Enkhuizen, Netherlands, since 2003. The distinctive characteristics of this new *Gaillardia* are stable and reproduced true to type in successive generations of asexual reproduction.

The new *Gaillardia* plant is a perennial in zones 4 to 9 in the US.

DESCRIPTION OF THE DRAWING

The new *Gaillardia* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Gaillardia.* The data which defines these characteristics were collected from asexual reproductions carried out in Enkhuizen, The Netherlands. The plant history was taken on 13 week old plants. The instant plant was grown in an 11 cm container in an outdoor container field.

Color references are primarily to the R.H.S. Colour Chart of The Royal Horticultural Society of London.

Plants of the new *Gaillardia* differ primarily from the plants of the originator 'Burgundy' in the following characteristics:

Flowers of the new variety are yellow colored whereas flowers of the originator are deep red colored. Plants of the new variety flower very early without needing cold for flower induction, whereas plants of the originator flower late and need cold for flower induction.

TABLE 1

DIFFERENCES BETWEEN THE NEW CULTIVAR 'GRANORAN' AND A SIMILAR CULTIVAR

| | 'Granoran' | 'Yellow Queen' (Not patented) |
|---|---|---|
| Plant habit | Very compact | Loose |
| Time of flowering | 10-12 weeks after potting | 14-18 weeks after potting |
| Flower color | 14B | 7C |

The plant:
*Classification.*—Botanical: *Gaillardia aristata.*
Parentage:
*Originator selection.*—'Burgundy' (Not patented).
Propagation:
*Type of cutting.*—Terminal cuttings.
*Time to initiate roots.*—6–12 days at 18° C.
*Time to produce a rooted cutting.*—2 weeks.
*Root description.*—Fine, fibrous and white in color.
Plant description:
*Form.*—Globular, symmetrical, mounded.
*Height.*—39–45 cm.

*Plant diameter.*—24 cm.
*Branching habit.*—Freely basal branching.

The stem:
*Shape.*—Cylindrical.
*Color.*—138A.
*Texture.*—Strigose.
*Length.*—18 cm.
*Diameter.*—3 mm.
*Internode length.*—14 mm.
*Quantity.*—Approximately 25 per plant.

The foliage:
*Type.*—Simple.
*Arrangement.*—Opposite, decussate.
*Number of leaves per stem.*—12.
*Size of leaf.*—Length: 53–87 mm. Width: 18–24 mm.
*Shape of leaf.*—Oblanceolate.
*Shape of apex.*—Acute.
*Shape of base.*—Attenuate.
*Texture.*—Pubescent.
*Margin.*—Entire.
*Fragrance.*—Present.
*Color.*—Upper surface: 137C. Lower surface: 137D.
*Petiole.*—Absent.
*Venation.*—Reticulate.

The flower:
*Natural flowering season.*—June until September.
*Flower type.*—Composite; disc and ray florets arranged acropetally on a capitulum.
*Form.*—Solitary.
*Appearance.*—Single flowers.
*Aspect.*—Facing upward or outward.
*Flower size.*—Diameter: 53 mm. Depth: 34 mm.
*Disc diameter.*—13 mm.
*Number of flowers per plant.*—260.
*Flower opening/closing behavior.*—Flowers stay open permanently.
*Fragrance.*—No fragrance.
*Bud* (*just before flowering*).—Shape: Oval. Diameter: 4 mm. Length: 1 cm. Color: N88A. Texture: Pubescent.
*Ray florets.*—Quantity: 22. Arrangement: Radiate. Shape: Elongated, cupped; 5 petals fused at the base. Length: 26 mm. Width: 10 mm. Apex: Acute. Base: Attenuate. Margin: Entire. Texture both sides: Glabrous. Color when fully opened Upper side: 14B. Lower side: 14C.
*Disc florets.*—Quantity: 76. Shape: Cylindrical, 6 acuminate lobes at apex. Length: 7 mm. Diameter: 1 mm. Texture: Glabrous. Color: 54C.
*Receptical.*—Shape: Cone. Diameter: 14 mm. Depth: 7 mm. Color: 144C.
*Peduncle.*—Form: Strong, erect. Length: 45 mm. Diameter: 2 mm. Texture: Strigose. Color: 143B.
*Involucral bracts.*—Quantity: 24. Shape: Lanceolate. Apex: Acuminate. Base: Truncate. Margin: Entire. Length: 7 mm. Width: 3 mm. Texture: Densely pubescent.
*Lasting quality of flowers.*—On the plant: 18 days. Cut flowers: 10 hours.

Reproductive organs:
*Androecium.*—On disc florets.
*Stamen number.*—4.
*Filaments.*—Adanate to corolla.
*Anther.*—Shape: Linear. Length: 2 mm. Color: 158D.
*Amount of pollen.*—Mediocre.
*Pollen color.*—164A.
*Gynoecium.*—On disc and ray florets.
*Stigma shape.*—2 parted.
*Stigma length.*—4 mm.
*Stigma color.*—158D.
*Pistil quantity.*—1 per floret.
*Pistil length.*—15 mm.
*Style length.*—4 mm.
*Color.*—158D.
*Ovary length.*—1 mm.
*Ovary color.*—145C.

Disease resistance: No disease/pest resistance has been observed to date.

Weather tolerance: Heat tolerant to 40° C.; susceptible to wet conditions.

Seed development: Seed development has not been observed to date.

What is claimed is:

1. A new and distinct cultivar of *Gaillardia* plant named 'Granoran,' as substantially illustrated and described herein.

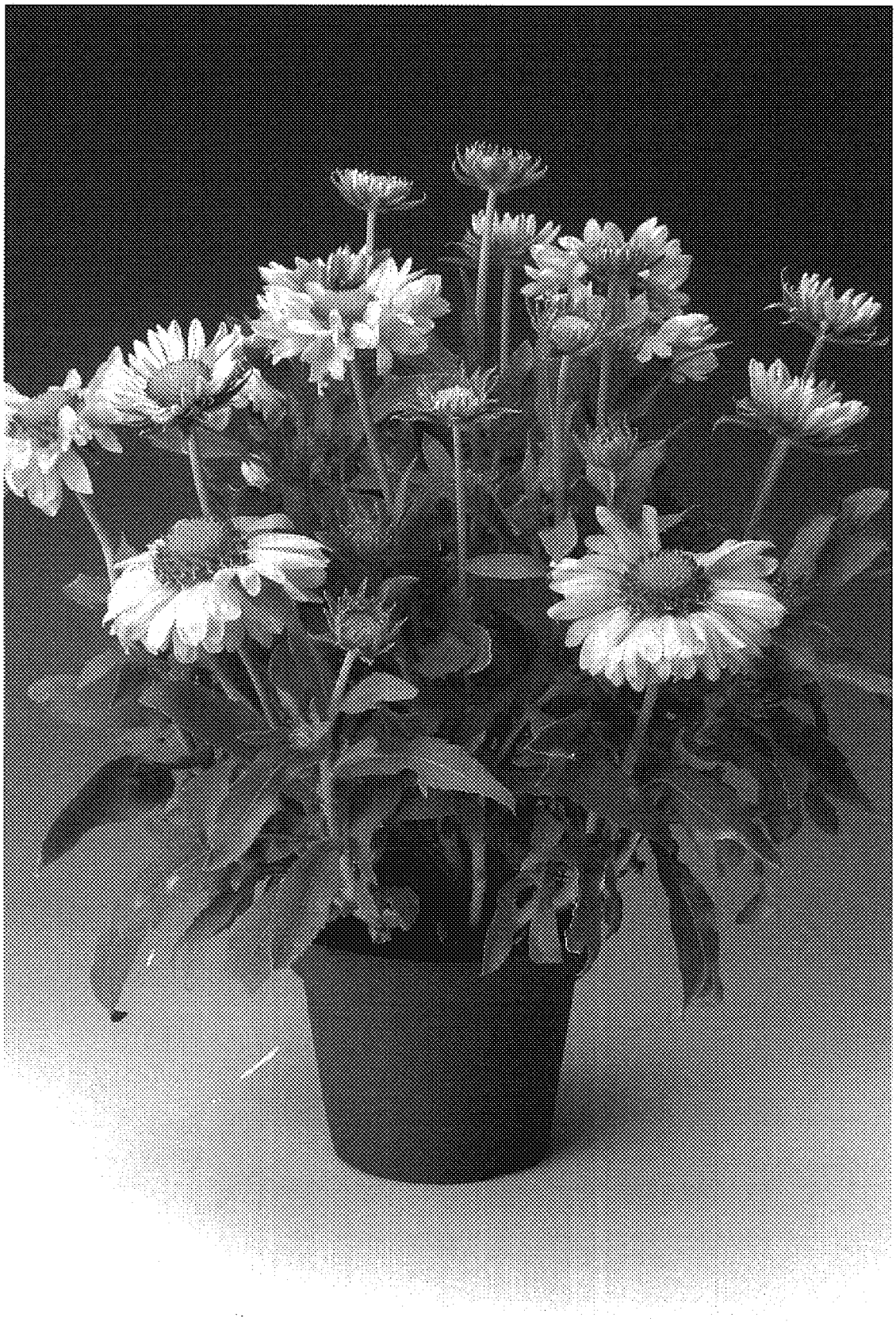

* * * * *